United States Patent [19]

Tovey et al.

[11] Patent Number: 5,330,501
[45] Date of Patent: Jul. 19, 1994

[54] TISSUE GRIPPING DEVICE FOR USE WITH A CANNULA AND A CANNULA INCORPORATING THE DEVICE

[75] Inventors: H. John Tovey, Milford, Conn.; Wayne P. Young, Brewster, N.Y.; David A. Nicholas, Trumbull, Conn.

[73] Assignee: United States Surgical Corporation, Norwalk, Conn.

[21] Appl. No.: 13,245

[22] Filed: Feb. 3, 1993

Related U.S. Application Data

[63] Continuation of Ser. No. 708,051, May 30, 1991, abandoned.

[51] Int. Cl.⁵ ............................................. A61M 29/00
[52] U.S. Cl. .................................. 606/198; 604/105; 604/164
[58] Field of Search .............. 604/104, 105, 127, 128, 604/164, 167, 168, 174, 264; 606/191, 192, 198

[56] References Cited

U.S. PATENT DOCUMENTS

| | | |
|---|---|---|
| 695,470 | 3/1902 | Milam . |
| 1,014,128 | 1/1912 | Crowe . |
| 1,045,906 | 12/1912 | Sweet . |
| 1,155,271 | 9/1915 | Philips . |
| 1,213,001 | 1/1917 | Philips . |
| 1,380,447 | 6/1921 | Wescott . |
| 1,434,964 | 11/1922 | Rose ................................. 604/109 |
| 2,001,638 | 5/1935 | Tornsjo . |
| 2,185,927 | 1/1940 | Shelanski . |
| 2,256,942 | 9/1941 | Duffy . |
| 2,338,800 | 1/1944 | Burke . |
| 2,496,111 | 1/1950 | Turkel . |
| 2,623,521 | 12/1952 | Shaw . |
| 2,705,949 | 4/1955 | Silverman . |
| 2,707,957 | 5/1955 | Sollmann . |
| 2,923,295 | 2/1960 | Guerriero . |
| 2,952,256 | 9/1960 | Meader et al. . |
| 3,030,959 | 4/1962 | Grunert . |
| 3,039,468 | 6/1962 | Price . |
| 3,330,268 | 7/1967 | Goldsmith . |
| 3,347,232 | 10/1967 | Ginsburg . |
| 3,459,189 | 8/1969 | Alley et al. . |
| 3,613,684 | 10/1971 | Sheridan . |
| 3,688,773 | 9/1972 | Weiss . |
| 3,707,146 | 12/1972 | Cook et al. . |
| 3,717,151 | 2/1973 | Collett ................................. 604/106 |
| 3,750,667 | 8/1973 | Pshenichny et al. . |

(List continued on next page.)

FOREIGN PATENT DOCUMENTS

| | | |
|---|---|---|
| 0232600 | 8/1987 | European Pat. Off. . |
| 0413493 | 2/1991 | European Pat. Off. . |
| 2218901 | 10/1973 | Fed. Rep. of Germany . |
| 748666 | 7/1933 | France . |
| 949943 | 9/1949 | France . |
| 475215 | 2/1951 | Italy . |
| 921554 | 4/1982 | U.S.S.R. . |
| 1521465 | 11/1989 | U.S.S.R. . |

OTHER PUBLICATIONS

An instruction sheet for the "Endopath Disposal Surgical Trocar and Sleeve" from Ethicon, Inc.
A brochure from Karl Storz Endoskope.

Primary Examiner—Stephen C. Pellegrino
Assistant Examiner—William W. Lewis

[57] ABSTRACT

A tissue gripping device for use with a cannula. The device includes a housing member which has a generally cylindrical shape and is provided with a plurality of slots about its circumference. A cannula locking collet and collar are provided along with a tissue gripping member so that the entire device fits over a cannula and is secured thereto. Once the cannula is positioned in the body wall of a patient, the tissue gripping member is moved towards the housing member so that a plurality of finger-like expansion members protrude through the slots in the housing member to anchor the tissue gripping device and the cannula in place for a surgical procedure.

26 Claims, 8 Drawing Sheets

U.S. PATENT DOCUMENTS

| | | | |
|---|---|---|---|
| 3,789,852 | 2/1974 | Kim et al. . | |
| 3,809,095 | 5/1974 | Cimber . | |
| 3,817,250 | 6/1974 | Weiss et al. . | |
| 3,817,251 | 6/1974 | Hasson . | |
| 3,824,556 | 7/1974 | Berkovits et al. . | |
| 3,860,006 | 1/1975 | Patel . | |
| 3,884,220 | 5/1975 | Hartnett . | |
| 3,886,946 | 6/1975 | Hyde . | |
| 3,993,079 | 11/1976 | Henriques de Gatztanondo . | |
| 4,043,346 | 8/1977 | Mobley et al. | 606/198 |
| 4,069,826 | 1/1978 | Sessions et al. | 604/105 |
| 4,077,412 | 3/1978 | Moossun . | |
| 4,083,370 | 4/1978 | Taylor . | |
| 4,177,814 | 12/1979 | Knepshield et al. . | |
| 4,186,750 | 2/1980 | Patel . | |
| 4,215,699 | 8/1980 | Patel . | |
| 4,230,123 | 10/1980 | Hawkins, Jr. . | |
| 4,299,230 | 11/1981 | Kubota . | |
| 4,419,094 | 12/1983 | Patel . | |
| 4,502,482 | 3/1985 | DeLuccia et al. . | |
| 4,535,773 | 8/1985 | Yoon . | |
| 4,601,710 | 7/1986 | Moll . | |
| 4,608,965 | 9/1986 | Anspach, Jr. et al. . | |
| 4,627,838 | 12/1986 | Cross et al. . | |
| 4,637,814 | 1/1987 | Leiboff . | |
| 4,654,030 | 3/1987 | Moll et al. . | |
| 4,670,008 | 6/1987 | Von Albertini . | |
| 4,941,882 | 7/1990 | Ward et al. . | |
| 4,973,305 | 11/1990 | Goltzer . | |
| 4,986,810 | 1/1991 | Semrad . | |
| 5,002,557 | 3/1991 | Hasson | 606/191 |
| 5,009,643 | 4/1991 | Reich et al. . | |
| 5,122,122 | 6/1992 | Allgood | 604/195 |

TISSUE GRIPPING DEVICE FOR USE WITH A CANNULA AND A CANNULA INCORPORATING THE DEVICE

CROSS-REFERENCE TO RELATED APPLICATIONS

This application is a continuation application of U.S. application Ser. No. 07/708,051 filed May 30, 1991 now abandoned.

BACKGROUND OF THE INVENTION

1. Field of the Invention

The present invention relates to surgical instruments for performing laparoscopic and endoscopic surgical procedures, and more particularly to devices for securing instruments such as cannulas in an incision in a patient's body during the surgical procedure.

2. Discussion of the Prior Art

In recent years, laparoscopic and endoscopic surgical procedures have become increasingly popular for performing major surgical operations In such a procedure, a small incision or puncture is made in the patient's body to provide access for a tube or a cannula device which is inserted into the patient's body to allow for viewing the surgical site and for the insertion of instruments used in performing the surgical procedure. Typically, a trocar device is used to penetrate the body wall, whereby a sharpened point or tip of the trocar assembly creates the path to the surgical site. A cannula is provided as part of the trocar assembly, so that when the pointed piercing mechanism is removed, the cannula remains in place to maintain access to the surgical site. Several incisions may be made to provide numerous access ports to the surgical objective, and once the cannulas are in place, various surgical instruments such as scissors, dissectors, retractors or the like, may be inserted by a surgeon to perform the surgery. Typically, a scope device is used to view the area directly, or a miniature camera is used to display the surgical site on a video monitor set up in the operating room.

The primary benefit of such minimally invasive surgical techniques is the reduction of scarring and consequently, minimizing damage to surrounding tissue and organs. As a consequence, recovery time is greatly reduced for the patient.

During a laparoscopic surgical procedure, gas is introduced into the body cavity by means of a pneumoperitoneum needle to inflate the cavity to provide greater access to the surgical area and minimize obstruction during surgery. The trocar assembly is then inserted into the body cavity, usually the abdomen, to a point adjacent the tissue or organ which is the surgical objective. After the pointed obturator is removed, the cannula remains in place in the patient's body. Due to the insufflation of the gas, it is necessary to maintain a gas seal at each of the cannulas in position in the body. It is also necessary to maintain the cannulas in a relatively immobile state, primarily to free the surgeon and the surgical assistants from having to hold the cannulas to prevent these instruments from backing off and consequently falling out of the incision. Furthermore, movement of the cannulas may result in a breakdown of the gas seal thereby negatively effecting the surgical procedure.

In order to maintain the integrity of the gas seal at the incision and to support the cannula in a hands-off manner, it has been known to provide various mechanisms and devices such as external sleeves which attempt to maintain and secure the cannula in the incision. However, many of these devices serve one function only, such as preventing unintentional removal of the cannula from the incision, or other functions such as limiting penetration of the cannula into the body cavity to prevent damage to tissues if the cannula is over-inserted.

Typical devices include penetration limiting devices such as the sleeve or collar disclosed in U.S. Pat. No. 3,817,251 to Hasson, which provides a conical sleeve which may be adjusted to various positions on the cannula to limit insertion of the cannula to specific depths. The sleeve positioned on the cannula provides some form of gas sealing, but only if the cannula is maintained in its fully inserted position, so that the sleeve is fitted into the incision. However, such a device provides no means for preventing the backing off of the cannula as the integrity of the gas seal may be compromised due to the movement of the cannula during the surgical procedure.

U.S. Pat. No. 4,077,412 to Moossun, as well as U.S. Pat. No. 4,627,838 to Cross et al., disclose devices to prevent the inadvertent removal or backing off of the cannula during the surgical procedure. Moossun provides an inflatable diaphragm member which is inflated once the cannula is positioned in the body cavity. The balloon type diaphragm prevents inadvertent removal of the cannula from the incision until the diaphragm is deflated. Cross et al. provide a complex wing-type mechanism which is extended once the catheter is positioned within the body cavity so that the wing members engage the body wall to prevent removal of the catheter until the wing mechanism is collapsed.

Also known in the prior art are sleeve members having external ribs, where the sleeve fits over the cannula and is forced into the incision either by twisting or simply by forcing the sleeve into the incision along with the catheter. Such devices may damage the surrounding tissue if improperly inserted, and if the sleeve is too large for the incision, may lead to tearing of the tissue.

The novel tissue gripping device for use with a cannula of the present invention obviates the disadvantages encountered in the prior art and provides a simple device for attaching to the cannula to hold the cannula in place during the surgical procedure to prevent inadvertent removal or over-insertion of the cannula into the body cavity. Alternately, the device may be constructed integrally with the cannula. The device of the present invention allows a surgical team to avoid having to hold the cannulas during a surgical operation, to free the surgical team to handle the implements necessary to effect the surgical objective. The device of the present invention also provides the required gas sealing necessary to perform laparoscopic surgical procedures.

SUMMARY OF THE INVENTION

The present invention provides a novel tissue gripping device for use with a cannula which supports the cannula in an incision in the patient's body to provide access to the abdominal cavity during a laparoscopic or endoscopic surgical procedure. The device also maintains the gas seal after the body cavity has been insufflated which is necessary to perform the surgical procedure. Tissue damage is minimized, and the device of the present invention secures the cannula in place to provide for hands-off support of the cannula in the body wall.

The tissue gripping device of the present invention may be used with various cannulas, or may be constructed integral with the cannula which is part of the trocar assembly which provides for penetration of the body wall during the surgical procedure. Such a construction reduces a number of instruments required in the operating room, thus increasing the efficiency of the surgical team.

The tissue gripping device of the present invention essentially comprises a housing member which is generally cylindrical in shape and which preferably tapers at its distal end to form a truncated conical shape to facilitate insertion through the body wall. A plurality of slots are provided which run generally longitudinally and are spaced about the outer wall of the housing equidistant from each other. Preferably, four slots are provided which afford access to the interior of the housing member. The proximal end of the housing member is provided with a gripping flange, and the interior of the flange is threaded to accept a locking collar. The locking collar may be provided with integral tabs which extend into the central passageway of the housing member, or the tabs may be provided on a separate collet member which is positioned on the housing member within the gripping flange prior to placement of the locking collar. The locking collar is provided with external threads which engage the inwardly directed threads on the housing member. The device of the present invention also includes a tissue gripping member which is generally cylindrically shaped and includes a plurality of finger-like flexible members which extend into the central passageway of the housing member and which correspond in number to the number of slots provided on the housing member. The finger members are dimensioned to align with and fit within the slots, and are provided with a camming surface at their distal end which engages a distal end wall of the slots to flex the expansion members outwardly.

In use, the device of the present invention is assembled with the collet and locking collar, as well as the tissue gripping member, nesting within the housing member. A trocar assembly, which includes a pointed obturator and a cannula body are then positioned within the tissue gripping device so that the cannula passes through the tissue gripping member, the locking collar, the collet and the housing member and extends through the distal opening of the housing member. The locking collar is then rotated in a tightening manner, so that the tabs of the collet engage the outer wall of the cannula to lock the housing member, the collet and the locking collar onto the cannula at a desired position. This position corresponds to the depth to which the surgeon wishes to insert the trocar assembly into the body cavity, although the locking collar may be loosened to re-position the tissue gripping device after the cannula is in place.

Once the cannula is inserted into the body, the tissue gripping member of the device of the present invention is then urged forwardly towards the body into the housing member. The camming surface of each of the finger-like expansion members engages the distal end wall of the slots which flexes the expansion members outwardly and into engagement with the tissue at the incision. The cannula, which is locked onto the housing member by the locking collar and collet mechanism is thereby secured in the incision by the outwardly deflected expansion members.

To remove the cannula, the tissue gripping member is withdrawn from the housing member so that the flexible nature of the expansion members draws the expansion members back through the slots, thus releasing the grip on the tissue and allowing the entire tissue gripping device and cannula to be withdrawn from the incision.

It is also contemplated that the device of the present invention be constructed as an integral part of the cannula of a typical trocar assembly. In such an assembly, the locking collar and collet device having the tabs for gripping the cannula will not be needed. In such an embodiment, the cannula itself would have a diameter sufficient to accept both the obturator and the tissue gripping member having the elongated flexible finger-like expansion members. The cannula itself preferably would include a plurality of slots through which the expansion members would extend, positioned about the circumference of the cylindrical cannula. Preferably, the cannula would taper at its distal end to facilitate penetration into the body, such that the inner diameter at the distal end would be slightly greater than the outer diameter of the obturator which passes therethrough. The tissue gripping member would be substantially identical to that described above, where the plurality of expansion members would extend into the cannula and terminate in camming surfaces which engage the distal end wall of the slots to flex the tissue contacting surfaces outwardly to secure the cannula in the tissue at the incision. To remove this device, the tissue gripping member would be slid rearwardly away from the body to withdraw the expansion members back into the cannula so that the cannula may be removed.

Alternately, the cannula may be provided with the finger-like expansion members mounted thereon, either integral to the construction of the cannula or fixedly and permanently secured thereto. In such an embodiment, a housing member as disclosed above would be provided which would slide over the cannula and expansion members so that as the cannula was inserted into the body, the camming surfaces of the expansion members would contact the distal end walls of the slots to flex the expansion members outwardly to grip the tissue. To remove the device, the entire cannula, and consequently the finger-like expansion members would be withdrawn from the body which would release the expansion members from the tissues so that the entire device may be removed.

In a further embodiment of the device of the present invention, the cannula includes a housing member fixedly secured over the distal end of the cannula by means of adhesives, sonic welding, staking or other means. The housing member includes the plurality of slots and has a truncated conical shape adjacent the distal opening of the cannula. A tissue gripping member is positioned over the cannula so that the finger-like expansion members extend into the slots in the concentric housing member. The cannula may be provided as an integral part of a trocar assembly, whose operation is similar to that described above.

BRIEF DESCRIPTION OF THE DRAWINGS

The foregoing features of the present invention will become more readily apparent and may be understood by referring to the following detailed description of an illustrative embodiment of the tissue gripping device for use with a cannula, taken in conjunction with the accompanying drawings, in which.

DETAILED DESCRIPTION OF THE PREFERRED EMBODIMENTS

Figure 1:
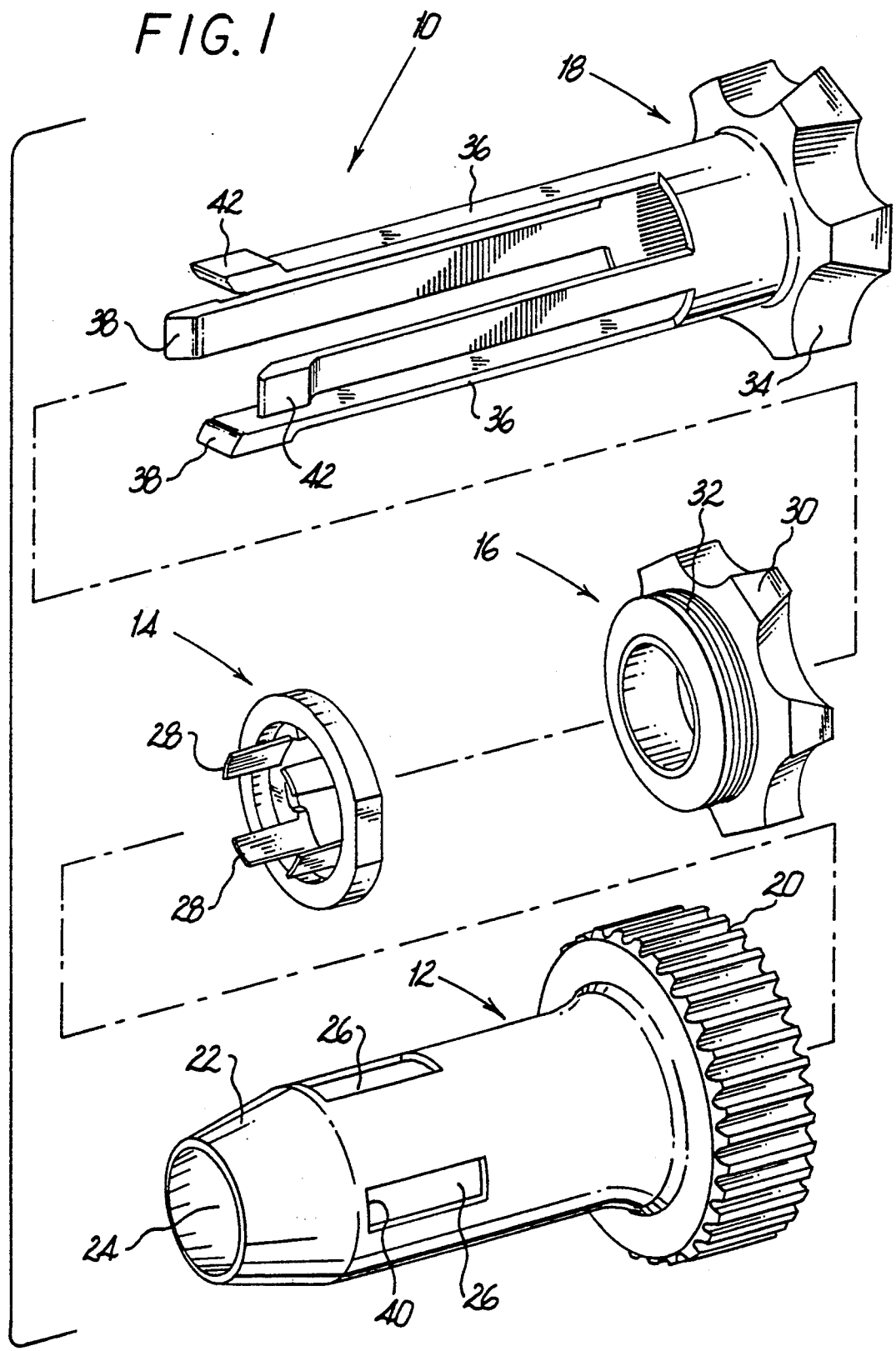
FIG. 1 illustrates the tissue gripping device of the present invention in an exploded perspective view.
Figure 2:
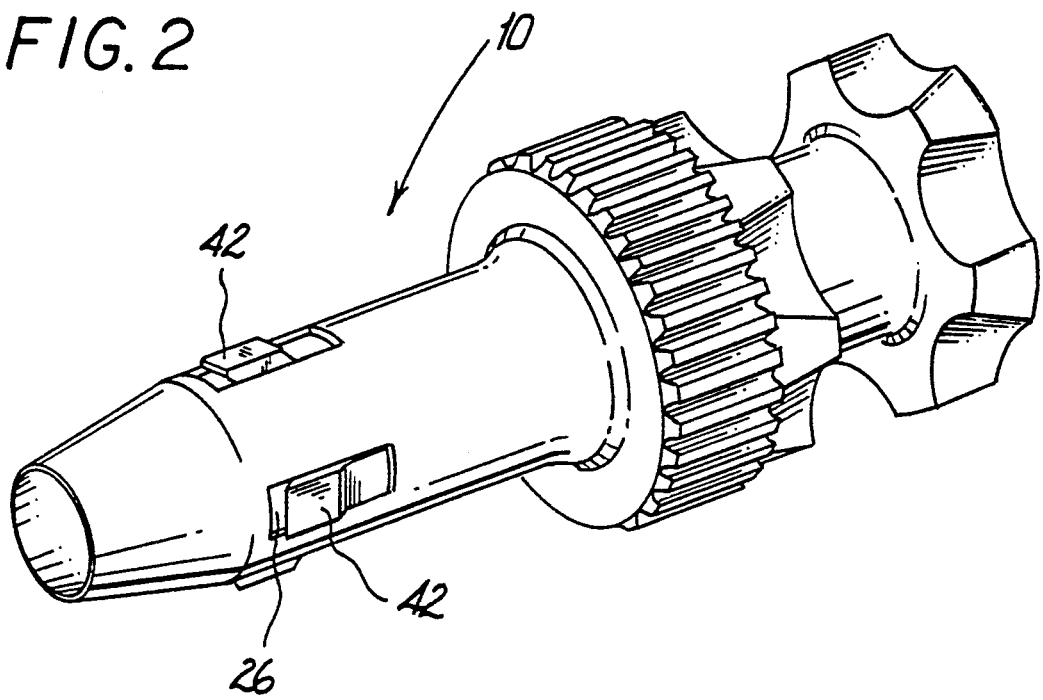
FIG. 2 illustrates the tissue gripping device of FIG. 1 in a fully assembled perspective view.

Referring now in specific detail to the drawings, in which like reference numerals identify similar or identical elements throughout the several views, FIGS. 1 and 2 show the tissue gripping device 10 of the present invention, where FIG. 1 illustrates the device in an exploded view while FIG. 2 shows the device in its fully assembled condition. Device 10 comprises a housing member 12, a cannula gripping collet 14, a lock collar 16, and a tissue gripping member 18 which passes through locking collar 16 and collet 14 into position within housing member 12. Housing member 12 has a generally cylindrical shape which extends from a proximal gripping flange 20, which remains outside the body during the surgical procedure. Housing member 12 preferably tapers at its distal end so that the distal end of housing member 12 has a truncated conical shape portion 22 adjacent distal opening 24. A plurality of slots 26 communicate with the interior of housing member 12, and slots 26 are spaced about the circumference of housing member 12 equidistant from each other. At least three slots 26 are provided, and in the preferred embodiment four slots 26 are provided.

Although not shown in FIGS. 1 and 2, proximal gripping flange 20 is provided with internal threads for accepting locking collar 16. As the device 10 is assembled, collet 14 is positioned inside proximal flange 20 and then locking collar 16 is loosely threaded into flange 20. Collet 14 is provided with cannula gripping tabs 28 whose function will be described below. Preferably, tabs 28 have an arcuate interior face to facilitate gripping a cannula positioned therein. Locking collar 16 is provided with gripping knob 30 and exteriorly directed threads 32 for securing locking collar 16 to housing member 12.

Tissue gripping member 18 has a generally cylindrical shape in which the outer diameter of tissue gripping member 18 is less than the inner diameter of collet 14, locking collar 16, and housing member 12, to allow tissue gripping member 18 to slide therethrough. A gripping knob 34 is provided, and a plurality of longitudinally extending flexible expansion members are provided, which correspond in number to slots 26 provided on housing member 12. Expansion members 36 are so dimensioned to allow their distal ends to be positioned within slots 26 and extend therethrough. Expansion members 36 are provided with a camming surface 38 and tissue contact faces 42 which contact tissue in the patient's body to anchor device 10 in place.

Figure 5:
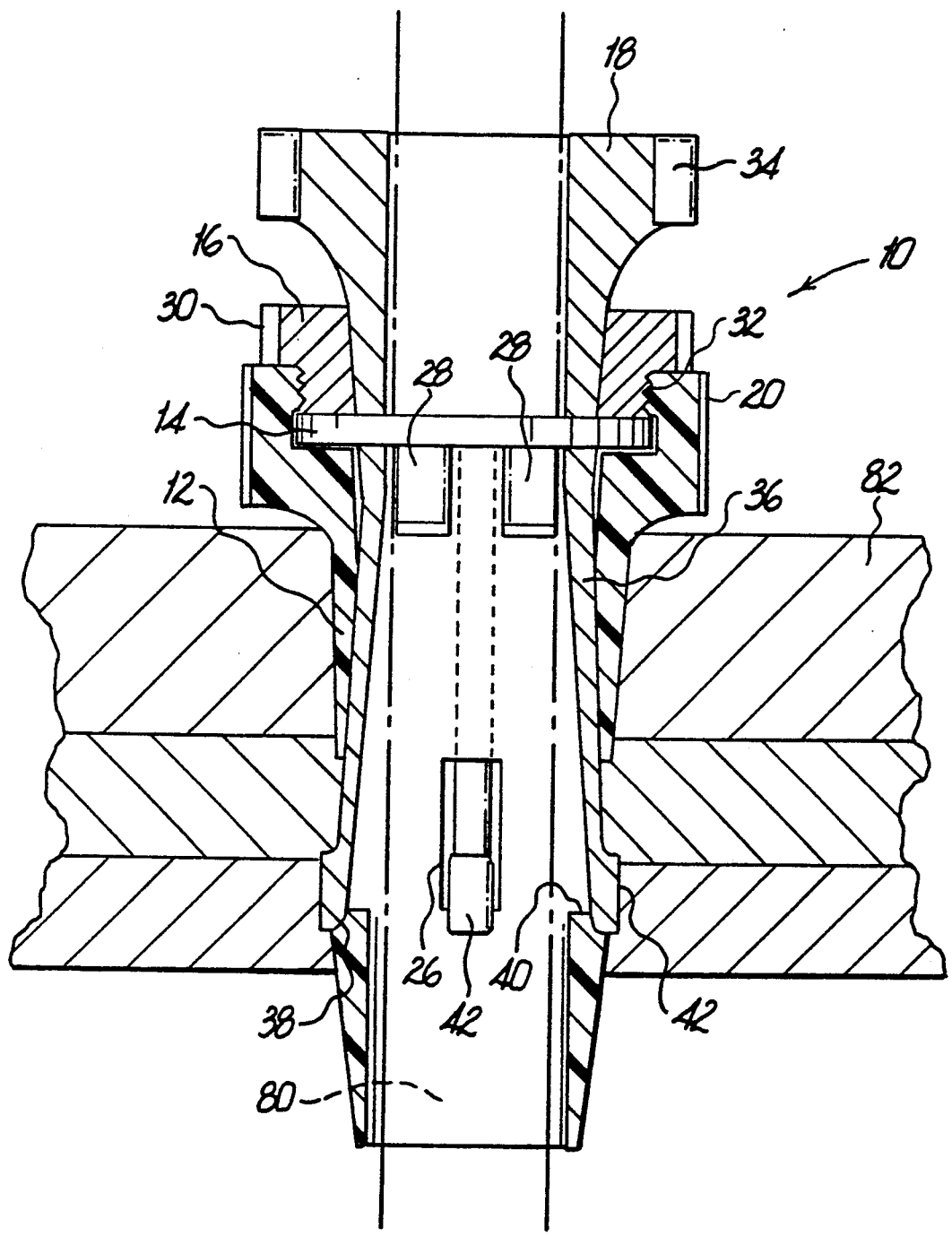
FIG. 5 illustrates a diagrammatic cross sectional view of the device of FIG. 1 in position in the body wall of a patient.

In use, it is best seen in FIG. 5, a cannula is positioned through device 10 so that it passes through housing 12, collet 14, locking collar 16 and tissue gripping member 18 as shown. As the cannula 80 penetrates the body tissue 82, locking collar 16 is loosely threaded onto housing member 12 at proximal flange 20 until cannula 80 is positioned at a desired surgical location. Locking collar 16 is then tightened by rotating gripping knob 30 to tighten collar 16 down onto collet 14. As locking collar 16 is tightened, a camming action occurs between the cannula gripping tabs 28 and the inner surface of housing member 12 to force cannula tabs 28 inwardly to contact and grasp cannula 80. Tightening locking collar 16 secures gripping tabs 28 to cannula 80 to hold device 10 onto cannula 80.

Once cannula 80 is in place with tissue gripping device 10 secured thereon, tissue gripping member 18 is slid in a direction towards the distal end of device 10. Camming surfaces 38 contact the end walls 40 of slots 26 and flex expansion members 36 outwardly so that tissue contact faces 42 expand outwardly into the tissue 82 to hold device 10 and cannula 80 in place. Expansion members 36 flex outwardly at an angle of between 10° and 25° relative to the longitudinal axis of device 10. Preferably, members 36 flex between 15° and 20° outwardly from their at rest position relative to the longitudinal axis to grip the tissue at the incision. To remove the cannula and tissue gripping device 10 from the tissue, tissue gripping member 18 is retracted so that expansion members 36 flex inwardly to release their grip on tissue 82.

Tissue gripping member 18 and expansion members 36 are constructed of plastic, preferably of a material having a rigid construction to provide the necessary gripping action after the members 36 flex outwardly to engage the tissue. Although many rigid plastic materials may be used, preferably housing 12 is constructed of polycarbonate, while acetal copolymer is utilized for gripping member 18. Such a material will provide a gripping force on the tissue that will enable the cannula to which gripping device 10 is secured to withstand a pull force of at least 25 lbs.

Figure 4:
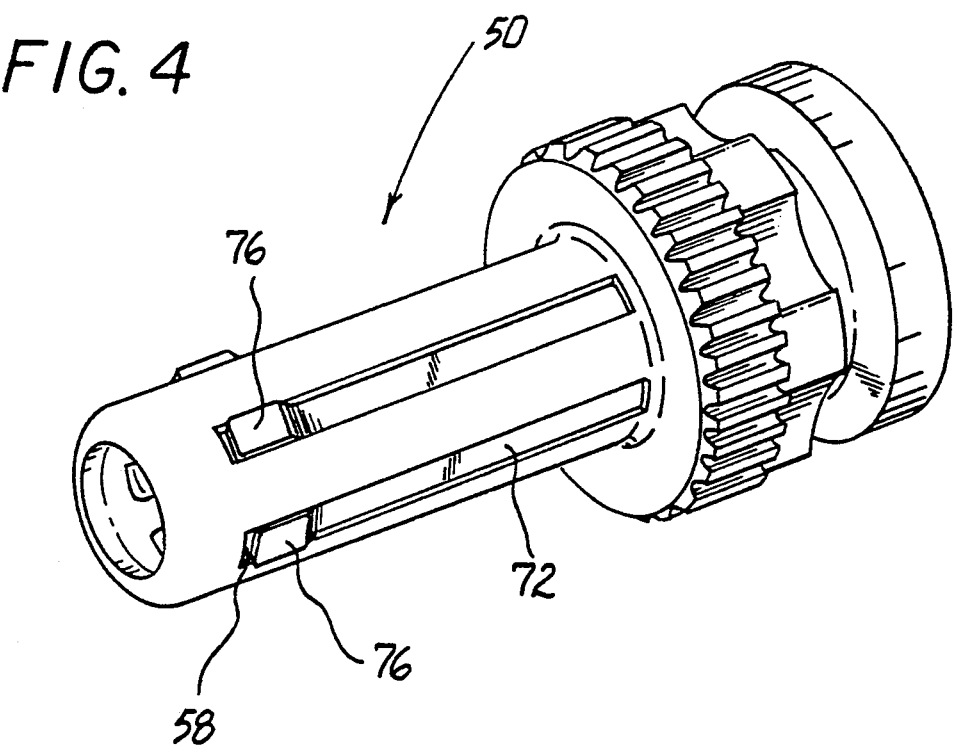
FIG. 4 illustrates the tissue gripping device of FIG. 3 in a fully assembled perspective view.
Figure 3:
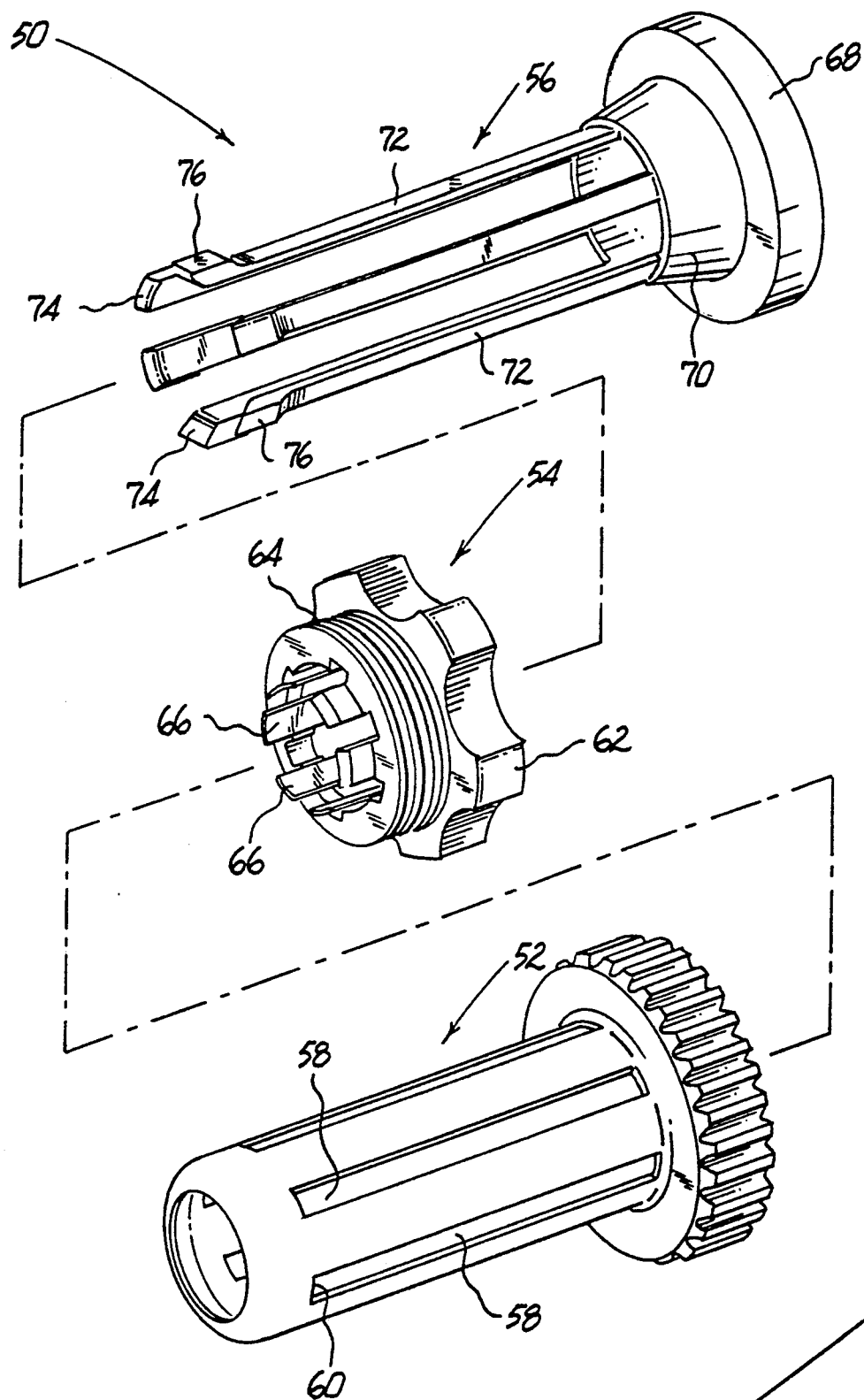
FIG. 3 illustrates an alternate embodiment of the tissue gripping device of the present invention in an exploded perspective view.

FIGS. 3 and 4 show an alternate embodiment of the tissue gripping device of the present invention. Tissue gripping device 50 is similar to tissue gripping device 10 except for the provision of additional expansion members and their corresponding slots. Furthermore, as best seen in FIG. 3, locking collar 16 and collet 14 are constructed as a single unit 54.

The device of FIGS. 3 and 4 comprise a housing member 52 having a generally cylindrical shape with a rounded distal end to facilitate penetration into the tissue. Housing member 52 is similar to housing member 12 except that slots 58 extend substantially the length of housing member 52 and terminate in end walls 60. Locking collet 54 comprises a gripping knob 62 and is provided with external threads 64 which engage internal threads on housing member 52 in the same manner as described above. Cannula gripping tabs 66 are provided as an integral part of locking collet 54. Tissue gripping member 56 includes a gripping flange 68 which tapers as shown at 70 towards expansion members 72. The diameter of tissue gripping member 56 is slightly less than the opening in locking collet 54 and the internal diameter of housing member 52. As shown in FIG. 3, six expansion members are provided, although any number may be provided. Preferably, at least three are provided to correspond in number and in substantial dimensions to slots 58. Each of expansion members 72 terminates in a camming surface 74 and in outwardly directed tissue contact face 76. As in FIG. 1, tissue contact face 76 lies in a plane which is essentially parallel to the longitudinal axis of tissue gripping device 50. Tissue gripping device 50 operates in substantially the same manner as tissue gripping device 10 as seen in FIG. 5.

Figure 6:
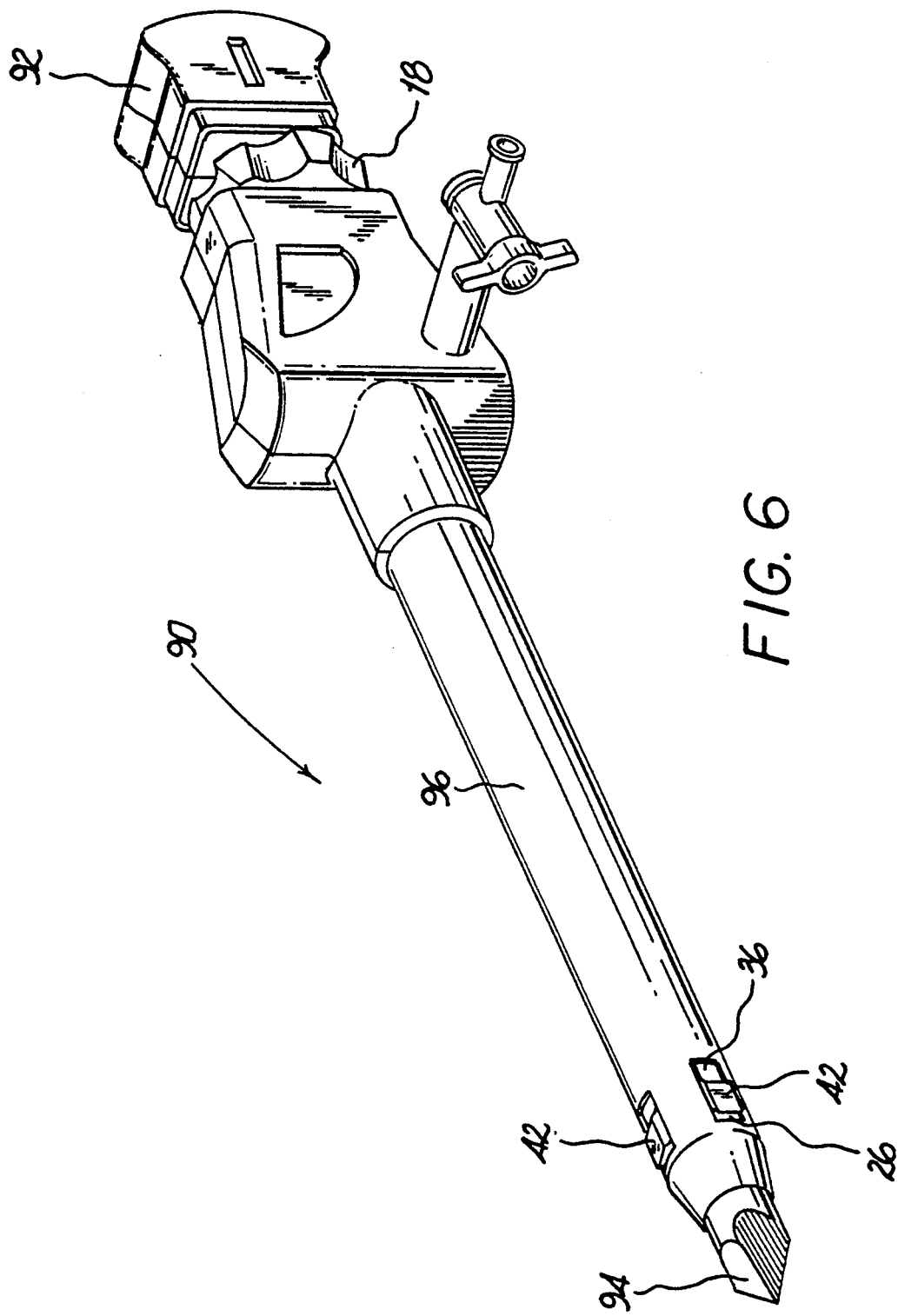
FIG. 6 illustrates a perspective view of a trocar assembly incorporating the tissue gripping device of the present invention.
Figure 7:
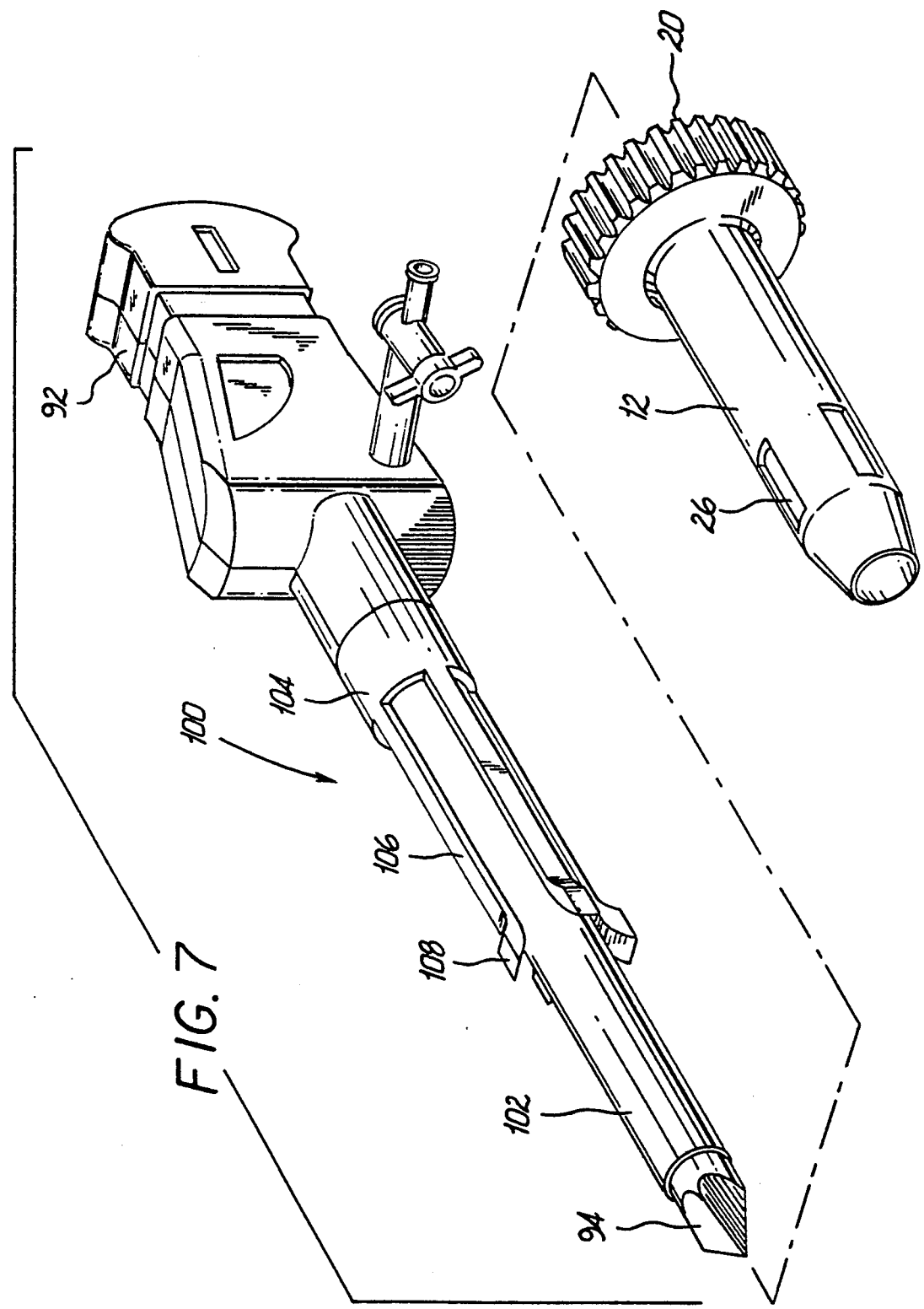
FIG. 7 illustrates an alternate embodiment of the trocar assembly of FIG. 6 incorporating the tissue gripping device of the present invention.

FIGS. 6 and 7 illustrate an alternate embodiment of the device of the present invention in which the tissue gripping device is made an integral part of a trocar assembly 90. As seen in FIG. 6, an obturator is provided having a gripping portion 92 and a pointed tissue penetrating tip 94. A cannula device 96 is provided which includes a plurality of slots 26 as described as in FIG. 1 above. A tissue gripping member 18 is provided which fits within cannula 96 and allows obturator 94 to pass therethrough. Tissue gripping member 18 terminates in tissue contact faces 42 of expansion members 36 and operates in the same manner as described above. After cannula 96 is secured in the tissue, the obturator is removed to provide access to the surgical site.

FIG. 7 shows an alternate embodiment of the trocar assembly of FIG. 6. Trocar assembly 100 is similar to trocar assembly 90 except that a tissue gripping member 104 is part of the cannula assembly 102. Tissue gripping member 104 may be an integral part of cannula 102, or may be fixedly secured thereto by, for example, a set screw, adhesives, etc. Tissue gripping member 104 is provided with a plurality of expansion members 106 which surround cannula 102 and terminate in tissue contact faces 108. A separate housing member 12 is provided which is identical to that described in reference to FIG. 1 above. After the device is secured in the patient's body wall, the obturator is removed and the cannula is secured in place as described above.

Figure 8:
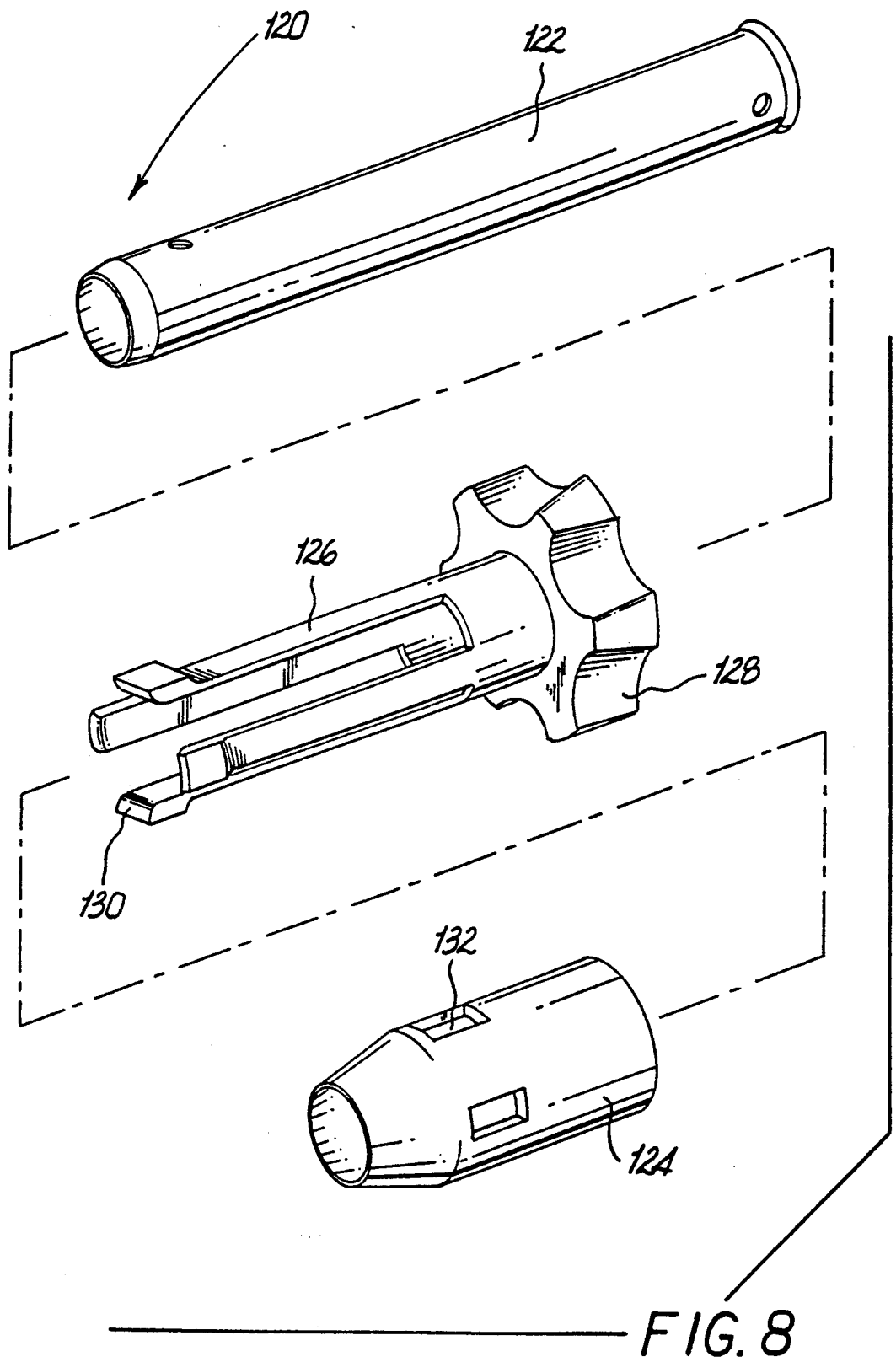
FIG. 8 illustrates an exploded perspective view of a further embodiment of a cannula incorporating the device of the present invention.
Figure 9:
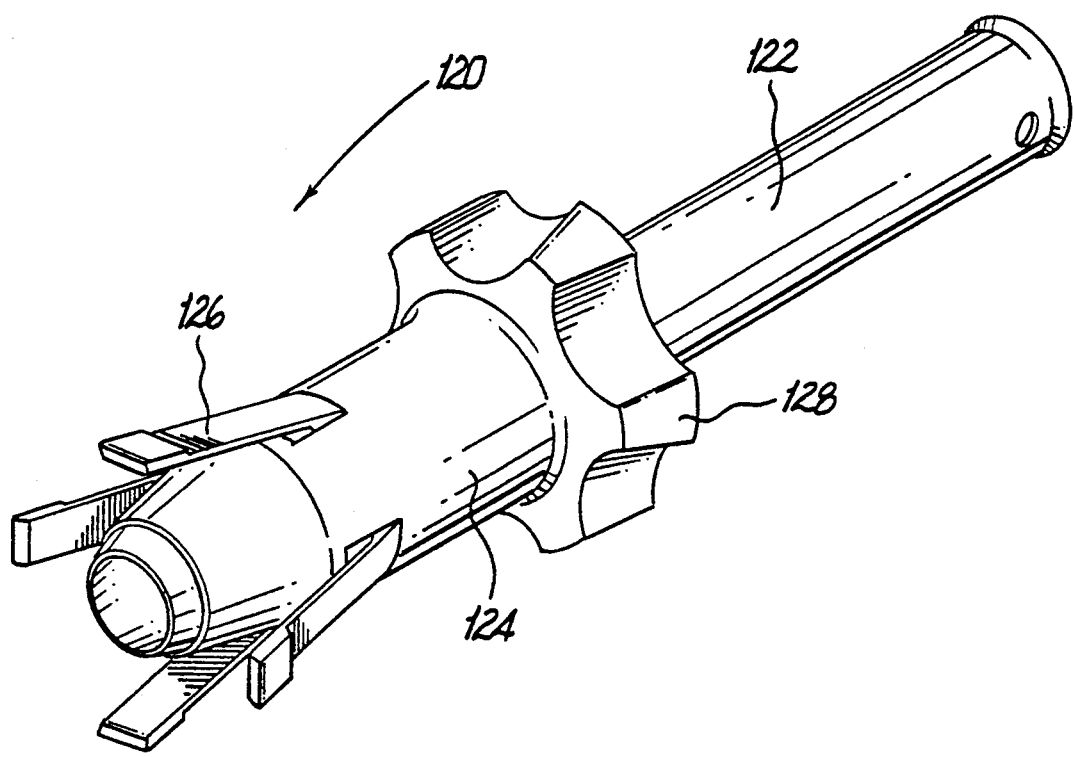
FIG. 9 illustrates a perspective view of the tissue gripping device of FIG. 8 in a fully assembled condition.

FIGS. 8 and 9 illustrate a further embodiment of the device of the present invention, in which the tissue gripping device is integral with a cannula, such as, for example, the cannula of a trocar assembly. Device 120 includes a cannula 122, to which a housing member 124 is fixedly secured. Housing member 124 is concentrically secured at a distal end of cannula 122 by conventional means, such as adhesives, heat staking, sonic welding, set screws, or the like. Housing member 124 preferably has a truncated conical end, and has a diameter at a proximal end which is greater than an outer diameter of cannula 122 for accepting the expansion members 126 of tissue gripping member 128. Tissue gripping member 128 is identical to tissue gripping member 18 described above, where expansion members 126 terminate in camming surfaces 130, which coact with slots 132 of housing member 124 to flex expansion members 126 outwardly as shown in FIG. 9 to engage tissue to hold cannula 122 in place. Device 120 is used as described above.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A tissue gripping device for use with a cannula, said device comprising:
    a housing member having a generally cylindrical shape including a central passageway, said housing member having flange means at a proximal end for positioning outside a patient's body and an opening at a distal end for positioning within said patient's body, said housing member having a plurality of longitudinally directed slots, said flange means including an internal threaded portion;
    a collet having a generally cylindrical shape including a central passageway aligned with said central passageway of said housing member, said collet having an external threaded portion adapted to cooperate with said threaded portion of said housing member, said collet further having means for engaging a cannula extending distally into said central passageway of said housing member when said collet is positioned thereon; and
    a tissue gripping member having a generally cylindrical shape including a plurality of flexible finger-like expansion members extending distally from a flange at a proximal end thereof, said members corresponding in number to said slots in said housing member, said members forming a cylinder having a first diameter such that said expansion members are positioned within said housing member;
    wherein said tissue gripping member passes through said collet into said housing member so that said finger-like expansion members align with said slots, such that advancing said gripping member distally into said housing member causes a distal end of said expansion members to contact a distal end of said slots to cam said members outwardly through said slots to engage tissue of patient.

2. A tissue gripping device according to claim 1, wherein said housing member tapers at said distal end to provide a truncated conical shape to said housing member at said distal end.

3. A tissue gripping device according to claim 2, wherein said slots in said housing member terminate adjacent said taper portion near said distal end.

4. A tissue gripping device according to claim 1, wherein said means for engaging a cannula comprises a plurality of gripping tabs on said collet having an inwardly directed face which has an arcuate shape corresponding to the shape of a cannula to facilitate gripping said cannula upon tightening.

5. A tissue gripping device according to claim 4, wherein said gripping tabs form a diameter which decreases as said collet is tightened by rotation into said housing member.

6. A tissue gripping device according to claim 1, wherein said collet has a gripping flange at a proximal end thereof to facilitate tightening.

7. A tissue gripping device according to claim 1, wherein said collet includes at least three gripping tabs, said tabs spaced equidistant from each other.

8. A tissue gripping device according to claim 1, wherein said tissue gripping member includes at least three expansion members spaced equidistant from each other.

9. A tissue gripping device according to claim 8, wherein said tissue gripping member includes no more than six expansion members.

10. A tissue gripping device according to claim 1, wherein said flange of said tissue gripping member comprising a gripping portion for grasping and moving said member.

11. A tissue gripping device according to claim 1, wherein said expansion members of said tissue gripping member are provided with an outwardly curving portion at said distal end, said curving portion comprising a camming surface to engage said distal end of said slots to cam said expansion members outwardly to engage said tissue.

12. A tissue gripping device according to claim 11, wherein said expansion members terminate in an outwardly facing tissue contacting surface, said surface being generally in the same plane as a longitudinal axis of said device.

13. A tissue gripping device according to claim 1, wherein said expansion members cam outwardly at an angle of between 10° and 25° relative to a longitudinal axis of said device.

14. A tissue gripping device according to claim 13, wherein said expansion members cam outwardly at an angle between 15° and 20° relative to said longitudinal axis.

15. A tissue gripping device according to claim 1, wherein expansion members engage said tissue at a force sufficient to withstand at least a 25 lb. pull force before disengaging from said tissue.

16. A tissue gripping device for use with a cannula, said device comprising:
   a tubular housing member having a distal opening and a proximal opening, said housing having a plurality of slots extending axially and spaced equidistant from each other about the circumference of said tubular housing;
   a cannula gripping collar positioned adjacent said proximal opening of said tubular housing member, said collar including a plurality of cannula gripping fingers extending into said tubular housing member, said collar having a central opening;
   a threaded locking collet engaging threads at said proximal opening of said tubular housing member for locking said collar and said housing member to said cannula upon rotation of said collet, said collet having a central opening;
   a tissue gripping member having a generally tubular shape including a plurality of flexible finger-like expansion members extending from a proximal knob-like member, said expansion members terminating at a distal end in tissue contacting surfaces which taper into camming surfaces, said plurality of expansion members corresponding in number to said slots in said housing member and being dimensioned to have a width slightly less than a width of said slots so as to flex through said slots, said gripping member having a central opening at said knob-like member slightly greater than a diameter of said cannula, and an outer diameter slightly less than the diameter of said housing member;
   wherein said tissue gripping member is movable from an at rest position where said expansion members are located within said housing member, to a gripping position where said tissue gripping member is advanced towards said distal end of said housing so that said camming surfaces contact said housing member at an end of each slot to expand the diameter of said expansion members by forcing said expansion members through said slots so that said tissue contacting surfaces engage tissue to anchor said device, and said cannula, in said tissue.

17. A tissue gripping device according to claim 16, wherein said housing member is tapered at its distal end to terminate in a truncated conical portion at said distal end.

18. A tissue gripping device according to claim 16, wherein said gripping fingers of said collar have an arcuately shaped inner face to facilitate contacting and gripping said cannula.

19. A tissue gripping device according to claim 16, wherein said collar includes at least three gripping fingers spaced equidistant from each other.

20. A tissue gripping device according to claim 16, wherein said gripping fingers of said collar contact an inner surface of said housing member upon tightening to move from a first at rest diameter to a second, cannula gripping diameter to secure to said cannula.

21. A tissue gripping device according to claim 16, wherein said housing member and said collet are each provided with a gripping flange at said proximal opening to facilitate gripping and tightening said collet to said housing member.

22. A tissue gripping device according to claim 16, wherein said tissue contacting surfaces of said expansion members lie in substantially the same plane as a longitudinal axis of said device.

23. A tissue gripping device according to claim 16, wherein said expansion members cam outwardly at an angle of between 10° and 25° relative to a longitudinal axis of said device.

24. A tissue gripping device according to claim 23, wherein said expansion members cam outwardly at an angle between 15° and 20°.

25. A tissue gripping device according to claim 16, wherein expansion members engage said tissue at a force sufficient to withstand at least a 25 lb. pull force before disengaging from said tissue.

26. A tissue gripping device for use with a cannula, said device comprising:
   a tubular housing member having a longitudinal passageway for accepting a cannula therein, said housing member having a plurality of slots disposed about the circumference of said housing member;
   means for releasably securing said housing member to said cannula to allow positioning of said housing member along said cannula;
   a tissue gripping member positioned within said housing member including a plurality of flexible finger-like expansion members corresponding in number to said slots and being extendable through said slots; and
   means for advancing said gripping member with respect to said housing member and said cannula to extend said expansion members through said slots.

* * * * *